(12) United States Patent
Klann (10) Patent No.: US 6,270,977 B1
(45) Date of Patent: *Aug. 7, 2001

(54) SPECIFIC, HIGHLY SENSITIVE, NESTED PCR DETECTION SCHEME FOR THE PSEUDORABIES VIRUS

(75) Inventor: Richard Chris Klann, Washington, NC (US)

(73) Assignee: Encelle, Inc., Greenville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/543,106

(22) Filed: Apr. 5, 2000

(51) Int. Cl.$^7$ .............................. C12Q 1/68; C07H 21/04; C07H 21/02; C12N 15/00
(52) U.S. Cl. ......................... 435/6; 536/23.1; 536/24.3; 935/76; 935/77; 935/78
(58) Field of Search ................................. 536/23.1, 24.3; 435/6, 91.2; 935/76, 77, 78

(56) References Cited

U.S. PATENT DOCUMENTS

| | | | |
|---|---|---|---|
| 4,683,202 | | 7/1987 | Mullis .................................... 435/91 |
| 5,449,765 | * | 9/1995 | Schreurs et al. . |
| 5,487,969 | | 1/1996 | Eberle et al. .............................. 435/5 |
| 5,545,523 | | 8/1996 | Batt et al. .................................. 435/6 |
| 5,798,265 | * | 8/1998 | Springer et al. . |
| 6,068,974 | * | 5/2000 | Klann . |

OTHER PUBLICATIONS

Robbins, et al., "*The Pseudorabies Virus gII Gene Is Closely Related to the gB Glycoprotein Gene of Herpes Simplex Virus*" Journal of Virology, vol. 61, No. 9, Sep. 1987, pp. 2691–2701.

Maes, et al., "*Polymerase Chain Reaction Amplification of Pseudorabies Virus DNA from Acutely and Latently Infected Cells*" Veterinary Microbiology, vol. 24, 1990, pp. 281–295.

Andrew K. Cheung, "*Detection of the Large Latency Transcript of Pseudorabies Virus by RNA–PCR and Its Potential in Diagnosis*" Journal of Veterinary Diagnostic Investigation, vol. 6, 1994, pp. 483–486.

Brown, et al., "*Detection of Pseudorabies Viral DNA in Tonsillar Epithelial Cells of Latently Infected Pigs*" American Journal of Veterinary Research, vol. 56, No. 5, May 1995, pp. 587–594.

Andrew K. Cheung, "*Investigation of Pseudorabies Virus DNA and RNA in Trigeminal Ganglia and Tonsil Tissues of Latently Infected Swine*" American Journal of Veterinary Research, vol. 56, No. 1, Jan. 1995, pp. 45–50.

Maes, et al., "*Recent Developments in Latency and Recombination of Aujeszky's Disease (Pseudorabies) Virus*" Veterinary Microbiology, vol. 55, 1997, pp. 13–27.

L.W. Enquist, PubMed Nucleotide Query, Accession No. M17321, Nov. 1987, pp. 1–3 (Computer–readable sequence), as published in Robbins, et al., "*The Pseudorabies Virus gII Gene Is Closely Related to the gB Glycoprotien Gene of Herpes Simplex Virus*" Journal of Virology, vol. 61, No. 9, Sep. 1987, pp. 2691–2701.

* cited by examiner

*Primary Examiner*—Ethan Whisenant
(74) *Attorney, Agent, or Firm*—Alston & Bird LLP (57) ABSTRACT

The present invention provides for a highly sensitive nested polymerase chain reaction (PCR) method for detecting the presence or absence of the pseudo rabies virus (PVR). The method targets a 674 base-pair region of the pseudorabies virus gII gene. Nucleotide sequences for highly specific novel primers derived from this gII region are also disclosed. These primers are used with the nested polymerase chain reaction method to amplify targeted nucleotide sequences within the 674 base-pair region of the gII gene. The novel primers and optimized reaction conditions of the nested polymerase chain reaction method enable significantly greater specificity for the viral DNA in tissue suspected of harboring the latent pseudorabies virus.

11 Claims, 5 Drawing Sheets

```
SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
          (A) LENGTH: 674 base pairs
          (B) TYPE: nucleic acid
```

(C) STRANDEDNESS: double
            (D) TOPOLOGY: linear (ii) MOLECULE TYPE: other nucleic acid
            (A) DESCRIPTION: /desc = "Region of the pseudorabies (vi) ORIGINAL SOURCE:
            (A) ORGANISM: Pseudorabies virus (xi) SEQUENCE DESCRIPTION: SEQ ID NO: 1:

GCCCCGCACA AGTTCAAGGC CCACATCTAC TACAAGAACG TCATCGTCAC GACCGTGTGG      60

TCCGGGAGCA CGTACGCGGC CATCACGAAC CGCTTCACAG ACCGCGTGCC CGTCCCCGT      120

CAGGAGATCA CGGACGTGAT CGACCGCCGC GGCAAGTGCG TCTCCAAGGC CGAGTACGT      180

CGCAACAACC ACAAGGTGAC CGCCTTCGAC CGCGACGAGA ACCCCGTCGA GGTGGACCT      240

CGCCCCTCGC GCCTGAACGC GCTCGGCACC CGCGGCTGGC ACACCACCAA CGACACCTA      300

ACCAAGATCG GCGCCGCGGG CTTCTACCAC ACGGGCACCT CCGTCAACTG CATCGTCGA      360

GAGGTGGAGG CGCGCTCCGT GTACCCCTAC GACTCCTTCG CCCTGTCCAC GGGGGACAT      420

GTGTACATGT CCCCCTTCTA CGGCCTGCGC GAGGGGGCCC ACGGGGAGCA CATCGGCTA      480

GCGCCCGGGC GCTTCCAGCA GGTGGAGCAC TACTACCCCA TCGACCTGGA CTCGCGCCT      540

CGCGCCTCCG AGAGCGTGAC GCGCAACTTT CTACGCACGC CGCACTTCAC GGTGGCCTG      600

GACTGGGCCC CCAAGACGCG GCGCGTGTGC AGCCTGGCCA AGTGGCGCGA GGCCGAGGA      660

ATGACCCGCG ACGA                                                      674

(2) INFORMATION FOR SEQ ID NO: 2:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Synthetic oligonucleotide"

(xi) SEQUENCE DESCRIPTION: SEQ ID NO: 2:

GCCCCGCACA AGTTCAA                                                    17

(2) INFORMATION FOR SEQ ID NO: 3:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Synthetic oligonucleotide"

(xi) SEQUENCE DESCRIPTION: SEQ ID NO: 3:

TCGCGGGTCA TCTCCTC                                                    17

(2) INFORMATION FOR SEQ ID NO: 4:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Synthetic oligonucleotide"

```
       (xi) SEQUENCE DESCRIPTION: SEQ ID NO: 4:

TCGTCGCGGG TCATCTC                                                          17

(2) INFORMATION FOR SEQ ID NO: 5:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "Synthetic oligonucleotide"

(xi) SEQUENCE DESCRIPTION: SEQ ID NO: 5:

TCACGAACCG CTTCACAGAC C                                                     21

(2) INFORMATION FOR SEQ ID NO: 6:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "Synthetic oligonucleotide"

(xi) SEQUENCE DESCRIPTION: SEQ ID NO: 6:

GCGGCAAGTG CGTCTCCAAG G                                                     21

(2) INFORMATION FOR SEQ ID NO: 7:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "Synthetic oligonucleotide"

(xi) SEQUENCE DESCRIPTION: SEQ ID NO: 7:

TGCGCAACAA CCACAAGGTG A                                                     21

(2) INFORMATION FOR SEQ ID NO: 8:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "Synthetic oligonucleotide"

(xi) SEQUENCE DESCRIPTION: SEQ ID NO: 8:

CTCCACCTCC TCGACGATGC                                                       20

(2) INFORMATION FOR SEQ ID NO: 9:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "Synthetic oligonucleotide"
```

-continued (xi) SEQUENCE DESCRIPTION: SEQ ID NO: 9:

CGTGGACAGG GCGAAGGAGT                      20

(2) INFORMATION FOR SEQ ID NO: 10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "Synthetic oligonucleotide"

(xi) SEQUENCE DESCRIPTION: SEQ ID NO: 10:

CGGCGTGCGT AGAAAGTTGC                      20

(2) INFORMATION FOR SEQ ID NO: 11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "Synthetic oligonucleotide"

(xi) SEQUENCE DESCRIPTION: SEQ ID NO: 11:

CGTGAAGTGC GGCGTGCGTA G                    21

SPECIFIC, HIGHLY SENSITIVE, NESTED PCR DETECTION SCHEME FOR THE PSEUDORABIES VIRUS

CROSS-REFERENCE TO RELATED APPLICATION

The present application is a continuation of U.S. Utility application Ser. No. 09/069,811, filed Apr. 29, 1998, herein incorporated by reference in its entirety.

FIELD OF THE INVENTION

The present invention relates to the use of a nested polymerase chain reaction (PCR) method for detection of viral organisms, more particularly to highly specific PCR primers and optimized reaction conditions for detecting the pseudorabies virus.

BACKGROUND OF THE INVENTION

Pseudorabies virus is a herpes virus belonging to the genus alphaherpesvirinae. Although most warm-blooded species can serve as a host, either through natural or experimental means, this virus primarily resides within the swine population. In its active state, pseudorabies virus causes a disease that is generally fatal to young pigs. Those animals surviving infection become lifelong carriers, harboring the virus in an inactive, noninfectious state. The latent virus can be reactivated to its infectious state within these carriers and spread to other susceptible animals. This inactivation-reactivation cycle leads to perpetuation of the virus within a swine herd.

The polymerase chain reaction (PCR) method (Mullis and Faloona (1987) *Meth. Enzymol.* 155:335–350) provides for the enzymatic amplification of rare DNA sequences and/or minute quantities of DNA, enabling detection of rare DNA sequences not possible by other methods. The technique has been successfully utilized to detect a number of viral agents, such as human immunodeficiency virus (HIV) (Kwok et al. (1987) *J. Virol.* 61:1690–1694; Laure (1988) *Lancet.* 2:538–541; Murakawa et al. (1988) *DNA* 7:287–295; Ou et al. (1988) *Science* 239:295–297); human papillomavirus (Shihata (1988) *J. Exp. Med.* 167:224–230); HSV (Rowley et al. (1990) *Lancet.* 335:440–441); human rhinovirus (Gama et al. (1988) *Nucleic Acids Res.* 16(19):9346); hepatitis B (Larzul et al. (1988) *J. Virol. Methods* 20:227–237); human T-cell leukemia (Kwok et al. (1988) *J. Infect. Dis.* 158:1193–1197; Bhagavati et al. (1988) *N. Engl. J. Med.* 318:1141–1147); and pseudorabies virus (Maes et al. (1997) *Vet. Microbiol.* 55 (1–4): 13–27).

The PCR technique is currently the preferred method for detecting the presence of latent pseudorabies virus in animals in the absence of detectable infectious virus (Cheung (1995) *Am. J. Vet. Res.* 56(1):45–50). Initially this method was restricted to trigeminal ganglia tissues, which were believed to be the primary site of the latent virus. More recently, standard PCR and nested PCR methods have been used to demonstrate that tonsilar mucosal cells also harbor the latent virus (Cheung (1995) *Am. J. Vet. Res.* 56(l):45–50; Brown et al. (1995) *Am J. Vet. Res.* 56(5):587–594).

Detecting the latent virus in tonsilar tissues even with present PCR methods available in the art remains difficult. The frequency of viral DNA and RNA in tonsilar tissues is lower than that seen for trigeminal ganglion tissues. Yet use of tonsilar tissues is preferable, as suspected carriers of the virus do not have to be euthanized to obtain the sample.

Greater specificity for the latent pseudorabies virus is needed to enable more efficient detection, particularly in tonsilar tissues. To this end, the present invention provides for highly specific PCR primers that are used in an optimized nested polymerase chain reaction to detect a highly sensitive region of the pseudorabies virus gII gene.

SUMMARY OF THE INVENTION

The present invention provides for a highly sensitive nested polymerase chain reaction (PCR) method for detecting the presence or absence of the pseudorabies virus. The method targets a region of the pseudorabies virus genome referred to as the gII gene, which encodes a glycoprotein essential for the virus's replication in the host. Nucleotide sequences for highly specific primers derived from the gII region are also disclosed. These primers are used in the nested polymerase chain reaction to amplify targeted nucleotide sequences within the gII gene.

The method of the present invention comprises: a) isolating a purified sample nucleic acid mixture from tissue suspected of being infected with the pseudorabies virus; b) mixing said sample with highly specific oligonucleotide primers derived from a 674 base-pair region of the pseudorabies virus gII gene to amplify targeted nucleotide sequences within the isolated nucleic acid mixture; and c) analyzing the amplified nucleotide sequences to detect the presence or absence of targeted nucleotide sequences comprising a specific region of the gII gene, where the presence of said targeted nucleotide sequences indicates the presence of the virus.

Kits useful in the practice of the invention are also provided.

DETA

The compositions of the present invention are nucleotide sequences comprising highly specific oligonucleotide primers that are synthesized from and hybridize to specific portions of a 674 base-pair region of the pseudorabies virus gII gene having the nucleotide sequence set forth in SEQ ID NO: 1. The gII gene encodes a glycoprotein that is essential for viral replication. The nucleotide sequence for this gene has been published (Robbins et al. (1987) *J Virology* 61:2691–2701; Accession No. M17321, herein incorporated by reference). The 674 base-pair region set forth in SEQ ID NO: 1 represents nucleotides 754–1427 of the published pseudorabies virus gII gene sequence (Accession No. M17321).

Primers for use in the invention are selected from a 674 base-pair region of the pseudorabies virus gII gene (see SEQ ID NO: 1). The nucleotide sequences for preferred primers of the present invention are set forth in SEQ ID NOS:2–11. These single-stranded primers are comprised of nucleotide sequences including naturally occurring nucleotides and any variants thereof. By "naturally occurring nucleotides" is intended adenosine triphosphate, guanosine triphosphate, cytosine triphosphate, thymidine triphosphate, uridine triphosphate, and inosine triphosphate. By "any variants thereof" is intended any nucleotides comprising modified bases of the form N6-(6-aminohexyl) (as in N6-(6-aminohexyl) dATP or N6-(6-aminohexyl) ATP), or comprising bases modified as 5'-thiol, 5'-phospho, 5'-methyl, 5'-biotinylated, 5'-amino, or 5'-fluoro (as in 5'-fluoro-deoxyadenosine). These primers are designed for desirable characteristics, including 3' ΔGs in the range of −6.3 to −8.5 and inability to form hairpin loops. Additionally, when any two of these primers are used as a primer pair for a polymerase chain reaction method according to the present invention, they do not hybridize to each other. A screening of the international bank of sequenced DNA has demonstrated that the primers of the present invention hybridize only to the 674 base-pair region of the pseudorabies virus gII gene. All of these characteristics enable a highly sensitive, highly specific nested polymerase chain reaction approach for detection of the pseudorabies virus in potentially infected samples.

Methods for the synthesis of these primers are available in the art. See particularly Sambrook et al. (1989) *Molecular Cloning: A Laboratory Manual* (2d ed.; Cold Spring Harbor Laboratory: Plainview, N.Y.), herein incorporated by reference.

In a second embodiment of the present invention, these primers are used in a nested polymerase chain reaction (PCR) method to detect the presence of the 674 base-pair region of the pseudorabies virus gII gene in a purified sample nucleic acid mixture, the nucleotide sequences of which have been extracted from a potentially infected sample. By "nested" PCR method is intended a two-staged polymerase chain reaction process. In a first-stage polymerase chain reaction, a pair of "outer" oligonucleotide primers, consisting of an upper and a lower primer that flank a particular first "target" nucleotide sequence in the 5' and 3' position, respectively, are used to amplify that first sequence. In a second-stage polymerase chain reaction, a second set of "inner" or "nested" oligonucleotide primers, also consisting of an upper and a lower primer, is used to amplify a smaller second "target" nucleotide sequence that is contained within the first target nucleotide sequence. The upper and lower inner primers flank the second target nucleotide sequence in the 5' and 3' positions, respectively. By "flanking primers" is intended primers that are complementary to segments on the 3'-end portions of the double-stranded target nucleotide sequence that is amplified during the PCR process. By "target" nucleotide sequence is intended a nucleotide sequence comprising a predetermined portion of the 674 base-pair region of the pseudorabies virus gII gene set forth in SEQ ID NO: 1. The base-pair size of these target nucleotide sequences and their particular position within the 674 base-pair region of the gene are determined by the pair of outer primers and pair of inner primers used in the first- and second-stage polymerase chain reactions, respectively.

By "amplify a target nucleotide sequence" is intended an increase by at least a factor of 100, preferably a factor of one million, more preferably a factor of ten million of the target sequence and an enrichment by at least a factor of 100, preferably a factor of one million, more preferably a factor of ten million of the target DNA concentration relative to the background DNA concentration.

Polymerase chain reaction (PCR) and nested PCR methods are available in the art. See generally Mullis (1987), U.S. Pat. No. 4,683,202; Eberle et al (1996), U.S. Pat. No. 5,487,969 (herpes B virus); Batt et al. (1996), U.S. Pat. No. 5,545,523 (bovine herpes virus-1); more particularly for the pseudorabies virus, see Maes et al. (1997) *Vet. Microbiol.* 55 (1–4): 13–27; Cheung (1994) *J. Vet. Diagn. Invest* 6:483–486; Cheung et al. (1995) *Am. J. Vet. Res.* 56(1): 45–50; Brown et al. (1995) *Am. J. Vet. Res.* 56(5):587–593; herein incorporated by reference.

The primers and nested PCR method of the present invention can be utilized for the detection of the presence or absence of the pseudorabies virus in any sample nucleic acid mixture isolated from any tissue sample suspected of harboring the pseudorabies virus. By "sample nucleic acid mixture" is intended a sample containing nucleic acids and mixtures thereof from any individual, strain, species, or genera of organism. Preferably the sample nucleic acid mixture is isolated from porcine tissue, more preferably from porcine tonsilar epithelial cells, as the latter material can be obtained from live animals.

The nested PCR method of the present invention comprises the following steps. A sample nucleic acid mixture is first isolated from a tissue sample suspected of being infected with the pseudorabies virus and then purified by centrifugation. Methods for isolation and preparation of the purified pseudorabies virus nucleic acid mixture are available in the art. See, for example, Robbins et al. (1987) *J. Virology* 61 (9):2691–2701; Maes et al. (1997) *Vet. Microbiol.* 55(1–4): 13–27; Cheung (1994) *J. Vet. Diagn. Invest.* 6:483–486; Cheung (1995) *Am. J. Vet. Res.* 56(1):45–50; and Brown et al. (1995) *Am. J. Vet. Res.* 56(5):587–593; herein incorporated by reference.

Using the highly specific oligonucleotide primers derived from the 674 base-pair region of the gII gene, targeted nucleotide sequences within the purified sample nucleic acid mixture (at least a portion of which will comprise nucleotide sequences from the gII gene when the tissue is infected) are amplified in an optimized nested PCR method. By "optimized" method is intended a method whose protocol has been modified repeatedly to determine the concentrations of reactants and experimental conditions that yield up to ≧about 10-fold, preferably≧about 100-fold, more preferably≧about 1,000-fold greater sensitivity for the pseudorabies virus than can be achieved using other PCR detection methods known in the art.

The nested PCR method of the present invention comprises the following steps. In a first-stage polymerase chain reaction, specific outer oligonucleotide primers are added to the sample nucleic acid mixture, and the resulting mixture is subjected to an initial denaturation step to obtain single-stranded DNA templates. Following denaturation, the mixture is subjected to an initial annealing step, where the outer primers hybridize to opposite strands of the first targeted nucleotide sequence. The temperature is then raised to allow for extension or replication of the specific segment of DNA across the region between the two primers by a thermostable DNA polymerase. The reaction is then thermocycled to allow for repeated denaturation, annealing, and extension, so that at each cycle, the amount of DNA representing the targeted nucleotide sequence between the two outer primers is doubled and the specific amplification of a first selected portion of the 674 base-pair region of the gII gene is amplified.

The first nucleotide sequence within the 674 base-pair region of the gII gene, which is targeted for amplification in the first-stage polymerase chain reaction, is flanked by an upper primer in the 5' upstream position and a lower primer in the 3' downstream position. The first targeted nucleotide sequence, and hence the amplification product of the first-stage polymerase chain reaction, has a predicted base-pair length, which is determined by the base-pair distance between the 5' upstream and 3' downstream hybridization positions of the upper and lower primers, respectively, of the outer primer pair. The upper and lower primers of the outer primer pair are derived from the 674 base-pair region of the pseudorabies virus gII gene (see SEQ ID NO: 1). For purposes of the present invention, the upper primer of the outer primer pair has the nucleotide sequence set forth in SEQ ID NO:2. The lower primer of the outer primer pair is preferably selected from the nucleotide sequences set forth in SEQ ID NOS:3 to 4, and more preferably is the nucleotide sequence set forth in SEQ ID NO:4.

At the end of the first-stage polymerase chain reaction, an aliquot of the resulting mixture is carried over into a second-stage polymerase chain reaction. In this second-stage reaction, the products of the first-stage reaction are combined with specific inner or nested primers. These inner primers are derived from nucleotide sequences within the first targeted nucleotide sequence and flank a second, smaller targeted nucleotide sequence contained within the first targeted nucleotide sequence. This mixture is subjected to initial denaturation, annealing, and extension steps, followed by thermocycling as before to allow for repeated denaturation, annealing, and extension or replication of the second targeted nucleotide sequence. This second targeted nucleotide sequence is flanked by an upper primer in the 5' upstream position and a lower primer in the 3' downstream position. The second targeted nucleotide sequence, and hence the amplification product of the second-stage PCR, also has a predicted base-pair length, which is determined by the base-pair distance between the 5' upstream and 3' downstream hybridization positions of the upper and lower primers, respectively, of the inner primer pair. The upper and lower primers of the inner primer pair are derived from within the 674 base-pair region of the pseudorabies virus gII gene (see SEQ ID NO: 1). For purposes of the present invention, the upper primer of the inner primer pair is preferably selected from the nucleotide sequences set forth in SEQ ID NOS:5 to 7, and more preferably is the nucleotide sequence set forth in SEQ ID NO:6. The lower primer of the inner primer pair is preferably selected from the nucleotide sequences set forth in SEQ ID NOS:8 to 11, and more preferably is the nucleotide sequence set forth in SEQ ID NO: 11.

The amplification products of the first- and second-stage polymerase chain reaction may be analyzed to identify the presence or absence of the first and second targeted nucleotide sequences comprising specific portions of the 674 base-pair region of the gII gene. Identification of the amplification products, as being derived from the pseudorabies virus gII gene, may be accomplished by any one of several methods known in the art to detect amplified nucleotide sequences. These methods include, but are not limited to, determination of size, restriction enzyme digestion pattern, subsequent cloning of amplification products, Southern blot hybridization with an oligonucleotide probe internal to the nucleotide sequence being amplified, or DNA sequencing.

The size of the product or products may be determined by electrophoresis through a gel, preferably an agarose gel, simultaneously with molecular size standards of known base-pair length. The gel may be stained with ethidium bromide, which intercalates between base pairs and enables the visualization of DNA upon illumination with ultraviolet light. In this manner, amplification products from the first- or second-stage PCR having equidistant migration with molecular size standards of approximately the base-pair length of the predicted first or second targeted nucleotide sequence, respectively, would verify presence of the pseudorabies virus gII gene, and hence the virus, within the original tissue sample.

Further verification of product specificity for a region within the pseudorabies virus gII gene may be performed by restriction endonuclease digest of the amplification products of the completed first- and second-stage polymerase chain reactions. Following digestion with restriction enzymes specific for known base-pair positions within the first or second targeted nucleotide sequence, the base-pair length of the digestion products may be determined using gel electrophoresis and ethidium bromide staining as described above. Depending upon the base-pair location of the restriction enzyme cut within the first- or second-stage PCR amplified nucleotide sequence, digestion would yield two nucleotide sequence fragments of predicted size. In this manner, digestion products from the first- or second-stage PCR amplified nucleotide sequences having equidistant migration with molecular size standards of approximately the base-pair length of the predicted nucleotide sequence fragments would verify presence of the pseudorabies virus gII gene, and hence the virus, within the original tissue sample.

Additional proof of sequence identity may be obtained by cloning of the first-stage polymerase chain reaction product. This reaction product can be ligated into any conventional plasmid vector for subsequent cloning in E. coi. Following an incubation period, plasmid DNA can then be isolated from transformed bacterial colonies, quantified with UV spectophotometry, and incubated with a desired restriction enzyme that removes the cloned insert from the plasmid backbone. The DNA fragments in the restriction digest can then be analyzed by gel electrophoresis as before to determine presence of the predicted first-stage polymerase chain reaction product.

Any method for identification of polymerase chain reaction products available in the art can be used with the present invention. See particularly Sambrook et aL (1989) *Molecular Cloning: A Laboratory Manual* (2d ed.; Cold Spring Harbor Laboratory: Plainview, N.Y.).

The present invention provides for "kits" comprising the elements necessary to detect the presence or absence of the pseudorabies virus in a sample using the nested PCR method of the invention. Such a kit may comprise a carrier being compartmentalized to receive in close confinement therein one or more container means, such as tubes or vials. One of said container means may contain at least two nucleotide sequences for an outer pair of oligonucleotide primers for use in a first-stage polymerase chain reaction, and at least two nucleotide sequences for an inner pair of oligonucleotide primers for use in a second-stage polymerase chain reaction. These outer and inner primer pairs, each consisting of a 5' upper primer and a 3' lower primer, are derived from the 674 base-pair region of the pseudorabies virus gII gene (SEQ ID NO: 1). For the purposes of the present invention, the upper primer of the outer primer pair has the nucleotide sequence set forth in SEQ ID NO:2; the lower primer of the outer primer pair is preferably selected from the nucleotide sequences set forth in SEQ ID NOS:3 to 4, and more preferably has the nucleotide sequence set forth in SEQ ID NO:4; the upper primer of the inner primer pair is preferably selected from the nucleotide sequences set forth in SEQ ID NOS:5 to 7, and more preferably has the nucleotide sequence set forth in SEQ ID NO:6; and the lower primer of the inner primer pair is preferably selected from the nucleotide sequences set forth in SEQ ID NOS:8 to 11, and more preferably has the nucleotide sequence set forth in SEQ ID NO: 11. These primers may be present in appropriate storage buffers.

One or more said container means of such a kit may contain one or more enzymes or reagents to be used in the nested PCR method of the invention. These enzymes may be present singly or in a mixture, in the lyophilized state or in an appropriate storage buffer. The kit may also contain any additional materials needed to carry out the detection method of the invention, such as buffers, extraction and purification reagents, nucleic acids, nucleotides (dNTPs), pipettes, plates, filter paper, gel electrophoresis materials, transfer materials, and the like.

The highly specific primer sequences and optimized reaction conditions of the nested polymerase chain reaction (PCR) method as disclosed in this invention enable up to ≧about 10-fold, preferably ≧about 100-fold, more preferably ≧about 1,000-fold greater sensitivity for the pseudorabies virus than can be achieved using other PCR detection methods known in the art. The sensitivity of this method allows for greater detection of the virus in the latent state, particularly within tonsillar tissues, before visible signs of viral disease are evident or after visible signs of disease have dissipated.

The following experiments are offered by way of illustration and not by way of limitation.

EXPERIMENTAL

Example 1
Synthesis of Oligonucleotide Primers

Highly specific oligonucleotide primers were synthesized from specific portions of a 674 base-pair region of the pseudorabies virus gII gene having the nucleotide sequence set forth in SEQ ID NO: 1. Nucleotide sequences for preferred primers (SEQ ID NOS:2–11) are shown in Table 1. Primers were ordered from Gibco BRL-Life Technologies, based on intended sequence, and purchased presynthesized. Although the single-stranded primers as shown were synthesized using naturally occurring nucleotides, any variant nucleotides could be used, particularly nucleotides comprising modified bases of the form N6-(6-aminohexyl) (as in N6-(6-aminohexyl) dATP or N6-(6-aminohexyl) ATP), or comprising bases modified as 5'-thiol, 5'-phospho, 5'-methyl, 5'-biotinylated, 5'-amino, or 5'-fluoro (as in 5'-fluoro-deoxyadenosine). A screening of the international bank of sequenced DNA demonstrated that these primers hybridize only to the 674 base-pair region of the pseudorabies virus gII gene.

Specificity and sensitivity of the nested PCR for the pseudorabies virus using preferred upper (SEQ ID NO:2) and lower (SEQ ID NO:4) outer primers and upper (SEQ ID NO:6) and lower (SEQ ID NO: 11) inner primers were tested as described in Examples 5 and 6. Other primers listed in Table 1 allow for selection of alternate primer pairs that are predicted to provide for a nested PCR having high specificity and high sensitivity for detection of the pseudorabies virus. These predictions are based on a comparison of their priming efficiencies with the priming efficiencies of the preferred primer pairs. The priming efficiency values are calculated by the software program used for primer design.

TABLE 1

Oligonucleotide primers specific for sequences of the pseudorabies virus gII gene

| oligonucleotide Sequences | Base-Pair Length | Gene Location |
|---|---|---|
| Outer Primers | | |
| GCCCCGCACAAGTTCAA SEQ ID NO:2 | 17 | nt 754–770 |
| TCGCGGGTCATCTCCTC SEQ ID NO:3 | 17 | nt 1424–1408 |
| TCGTCGCGGGTCATCTC SEQ ID NO:4 | 17 | nt 1427–1411 |
| Inner Primers | | |
| TCACGAACCGCTTCACAGACC SEQ ID NO:5 | 21 | nt 836–856 |
| GCGGCAAGTGCGTCTCCAAGG SEQ ID NO:6 | 21 | nt 902–922 |
| TGCGCAACAACCACAAGGTGA SEQ ID NO:7 | 21 | nt 932–952 |
| CTCCACCTCCTCGACGATGC SEQ ID NO:8 | 20 | nt 1122–1103 |
| CGTGGACAGGGCGAAGGAGT SEQ ID NO:9 | 20 | nt 1164–1145 |
| CGGCGTGCGTAGAAAGTTGC SEQ ID NO:10 | 20 | nt 1335–1316 |
| CGTGAAGTGCGGCGTGCGTAG SEQ ID NO:11 | 21 | nt 1344–1324 |

Example 2
Preparation of Purified Nucleic Acid Mixture from a Porcine Tonsilar Tissue Positive for the Pseudorabies Virus Field isolates of porcine tonsilar tissue were obtained from animals suspected of harboring the pseudorabies virus. Presence of the virus was confirmed via direct immunofluorescence screening, which was performed at National Veterinary Services Laboratory, Ames, Iowa. Upon receipt, half of each sample was stored at −80° C. The remaining portion was homogenized in GIT, a guanidine isothiocyanate-based extraction buffer (4 M guanidine isothiocyanate, 25 mM sodium acetate, and 120 mM 2-mercaptoethanol), with the use of a Dounce homogenizer.

Eight ml of each homogenized sample was layered onto 4 ml 5M CsCl and centrifuged at 32,000 RPM (182,400×g)

in a Beckman L8-70 for 23 hours. The upper 8 ml of the resulting gradient was discarded, and the lower 4 ml, which contained the sample DNA, was retained for further purification. The DNA was precipitated from solution by addition of 11 ml $H_2O$ and 35 ml 100% ethanol and then centrifuged at 10,000 xg for 15 minutes. The resulting precipitate of proteins, DNA, and salts was resuspended in TE buffer (10 mM Tris, 0.1 mM EDTA, pH 8.0 ) and incubated in the presence of 1 mg/ml proteinase K and 5% sodium dodecyl sulfate (SDS) at 65° C. for 15 minutes, then 37° C. for 3 hours.

Next, the sample solution was subjected to two rounds of addition of equal volume phenol:chloroform:isoamyl alcohol (PCI), centrifugation at 12,000 xg, and removal of the organic layer. After the second round of PCI, the DNA in the organic layer was precipitated with ⅒th volume 3 M sodium acetate and two volumes 100% ethanol. The precipitate was pelleted via centrifugation at 15,000 xg for 30 minutes, washed twice with 70% ethanol, air dried, and resuspended in TE buffer, pH 8.0. DNA quantification was performed by measuring the absorbance (A) of a given dilution (dilution factor, D.F.) of the sample at 260 nm, then at 280 nm, and the concentration calculated by the following formula: (D.F.)*(0.05)*(A260) =concentration in $\mu g/\mu l$.

Example 3
Nested PCR Assay for Detection of the Pseudorabies Virus

Figure 1:
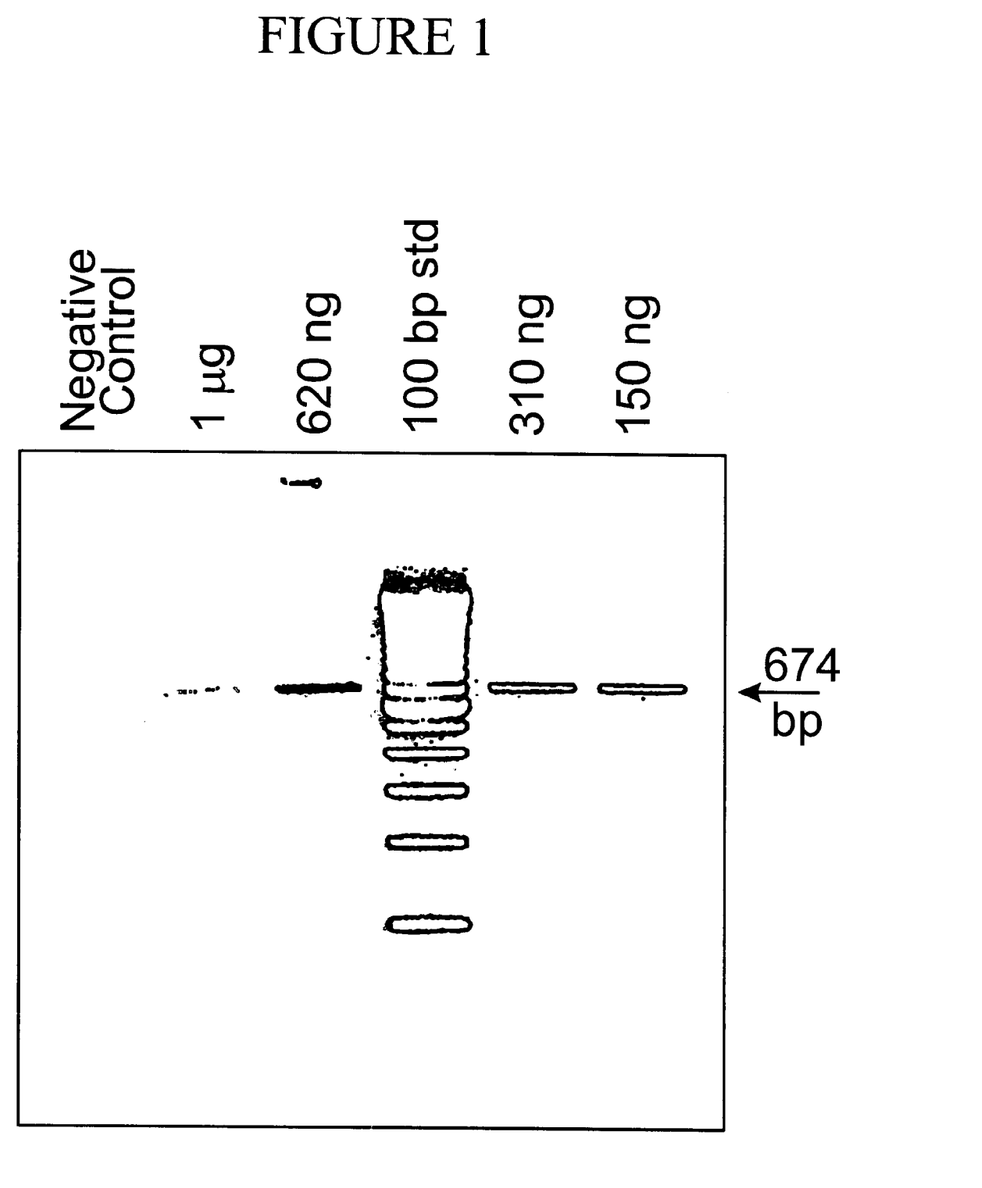
FIG. 1 represents an agarose gel showing the 674 base-pair product from the first-stage polymerase chain reaction. Purified DNA from PRV-infected porcine tonsil was used as template at the concentrations indicated.
Figure 2:
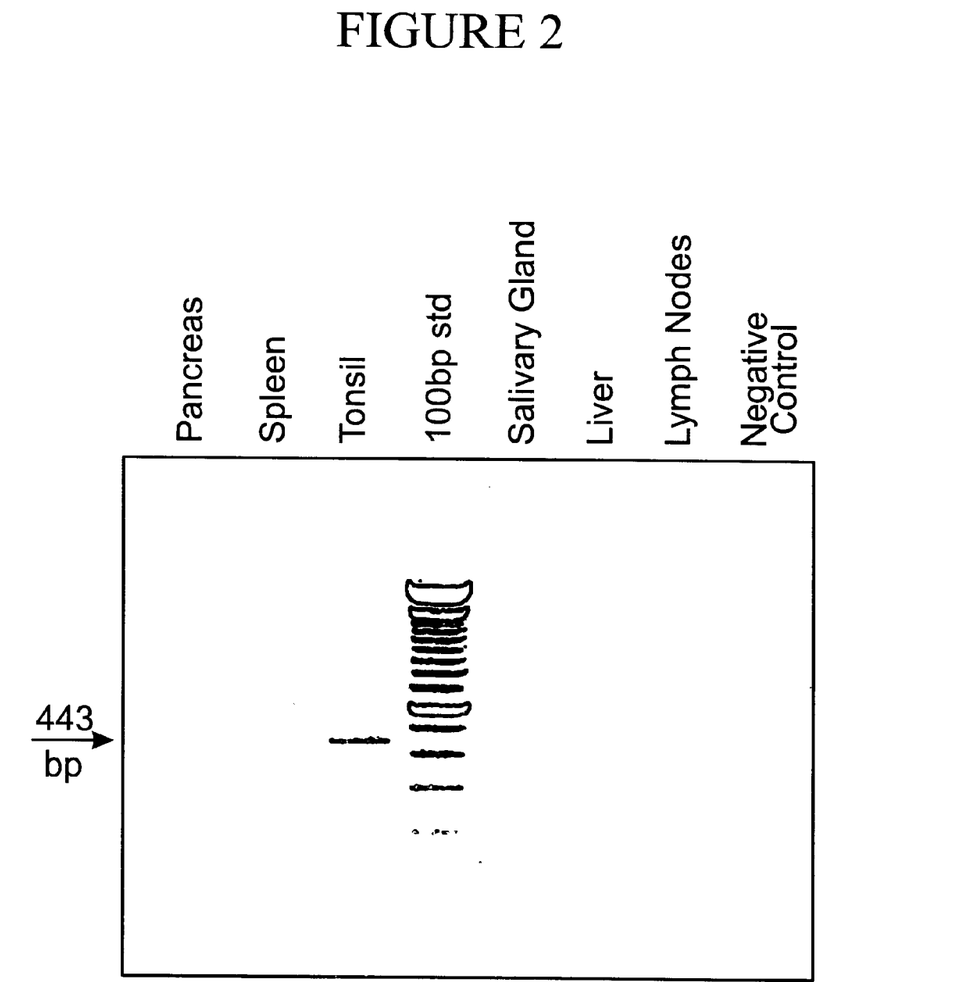
FIG. 2 represents an agarose gel showing the 443 base-pair product from the second-stage polymerase chain reaction. Purified DNA (1 µg) from several porcine tissues was used as template. A water-only blank served as the negative control.
Figure 3:
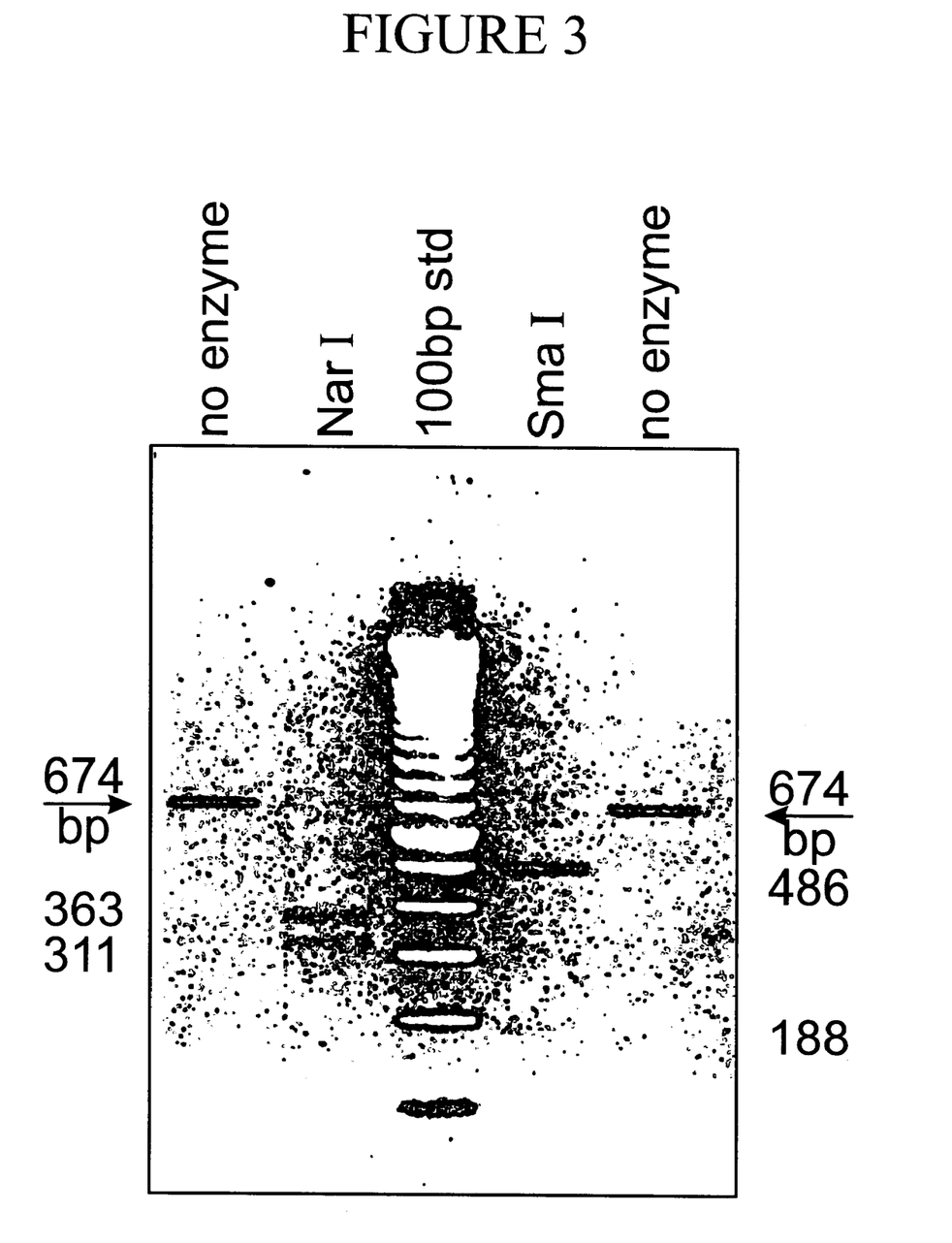
FIG. 3 illustrates confirmation of first-stage PCR product sequence identity by restriction enzyme digestion. Digestion with either Nar I or Sma I yielded fragments of the size expected based on the position of the specific recognition site for each enzyme in the published gene sequence.
Figure 4:
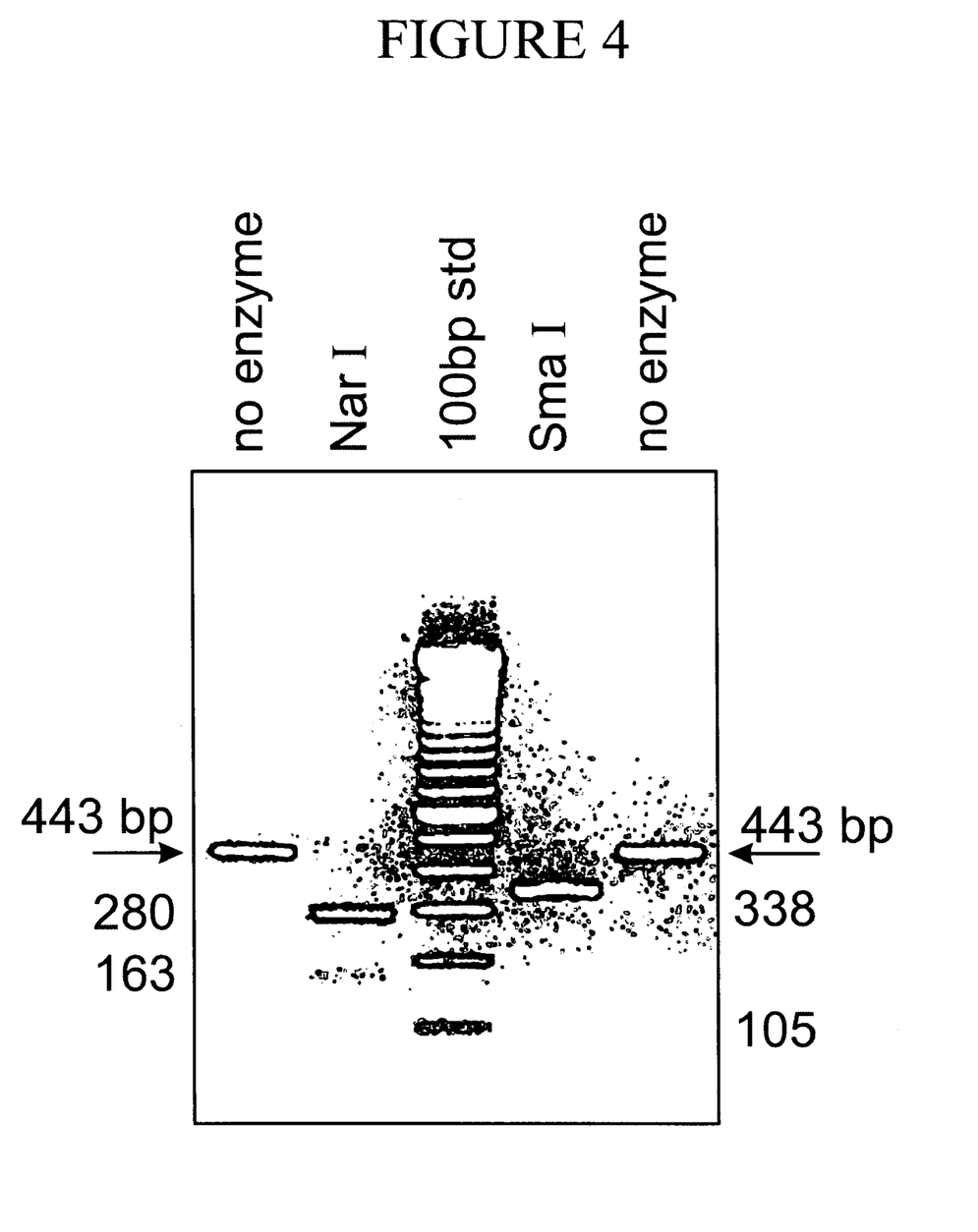
FIG. 4 illustrates confirmation of second-stage PCR product sequence identity by restriction enzyme digestion. Digestion with either Nar I or Sma I yielded fragments of the size expected based on the position of the specific recognition site for each enzyme in the published gene sequence.
Figure 5:
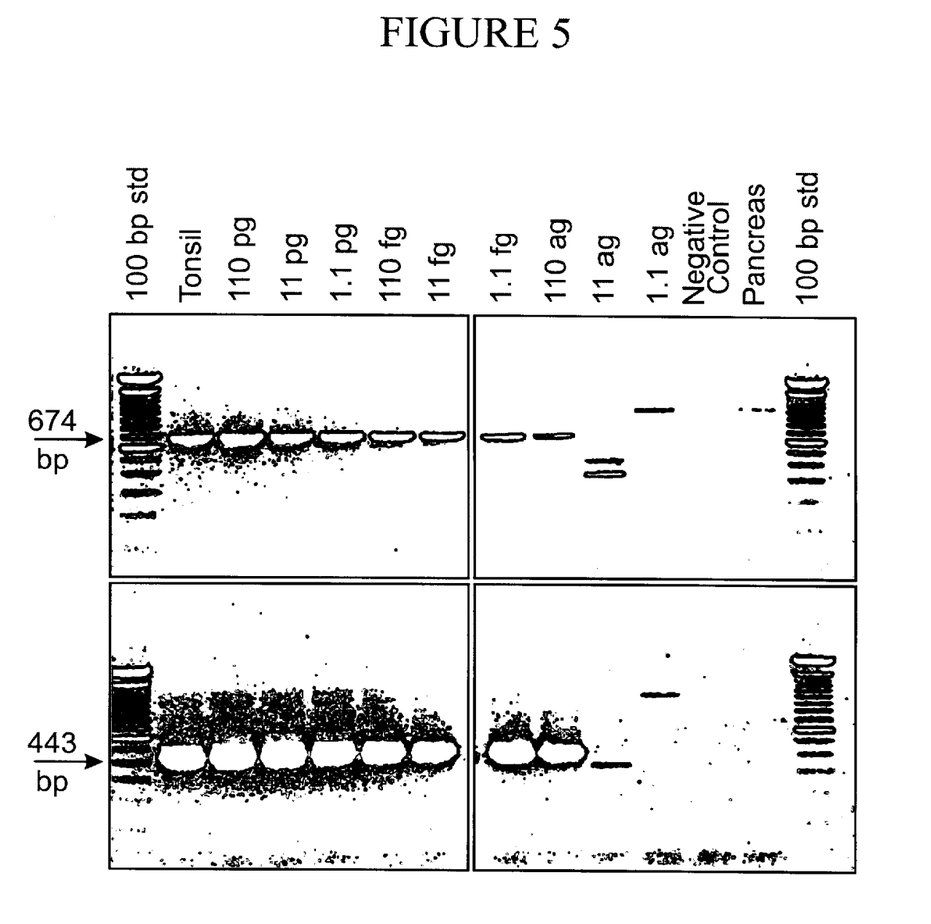
FIG. 5 demonstrates sensitivity of the optimized PCR assay for both the first-stage (upper panels) and the second-stage (lower panels) PCR reactions. Plasmid DNA at the concentrations indicated was spiked into reaction mixtures containing 1 µg of porcine pancreas DNA. Both a water blank and a reaction containing unspiked pancreas DNA served as negative controls. The gels show persistence of specific PCR amplification product with as little as 110 attograms of spiked PRV plasmid DNA, representing the equivalent of approximately 20 organisms.

From the gII sequence, outer and inner primer pairs were synthesized as in Example 1. These primer pairs were designed to fulfill certain characteristics enabling a highly sensitive and highly specific nested PCR approach. The upper and lower outer primers were predicted to produce a 674 base-pair (bp) amplified product (referred to as the N1 amplified product) in a first-stage polymerase chain reaction. The nucleotide sequences for these primers are listed 5' to 3' by location as follows: 754—GCCCCGCACAAGTTCAA (upper primer; SEQ ID NO:2) and 1427 —TCG TCG CGG GTC ATC TC (lower primer; SEQ ID NO:4). The upper and lower internal primers were predicted to produce a 443 bp amplified product (referred to as the N2 amplified product). The nucleotide sequences for these primers are listed 5' to 3' by location as follows: 902—GCG GCA AGT GCG TCT CCA AGG (upper primer; SEQ ID NO:6) and 1344—CGT GAA GTG CGG CGT GCG TAG (lower primer; SEQ ID NO: 11).

Following DNA quantification, 1 μg of each purified nucleic acid mixture sample was mixed with an appropriate quantity of first-stage (N 1) PCR master mix (see Example 4 below for formulation) to Q.S. to 50 μl. This and the second-stage PCR master mix consisted of a buffered solution containing optimum concentrations of nucleotides (dNTP), upper and lower PCR primers, and Taq DNA polymerase as determined in Example 4. Using a thermocycler, the resulting sample solution was then subjected to an initial denaturation step of 94° C. for 2 minutes, followed by 45 thermocycles of 94° C. for 30 seconds and 68° C. for 90 seconds. These steps allow for repeated cycles of separation of complementary strands of nucleic acids; annealing of primers to the 5' ends of separated complementary strands; and extension of the primers by DNA polymerase annealing complementary dNTPs together to form primer extension products across the region between the two primers. This process repeatedly replicates the targeted nucleotide sequence. At the end of the $45^{th}$ cycle, a final extension at 72° C. for 7 minutes was performed.

The resulting first-stage PCR solution for each sample was then subjected to a second-stage polymerase chain reaction using the nested or inner primer pairs described above. In this step, 2 μl of the completed N1 PCR solution containing the N1 amplified nucleotide sequence was carried over into 48 μl of the second-stage (N2) PCR master mix (see Example 4 below for formulation). The resulting sample solution was then thermocycled exactly as before with the following exceptions: the annealing step was at 70° C. for 30 seconds, and only 35 cycles were performed.

Example 4

Optimization of the Nested PCR Assay for the Pseudorabies Virus

The nested PCR assay described in Example 3 had been optimized to provide≧about 10-fold, preferably≧about 100-fold, more preferably≧about 1,000-fold greater sensitivity for the pseudorabies virus than can be achieved using other PCR detection methods known in the art. Optimization involved modification of standard PCR protocol available in the art. (See particularly "Guide to Optimizing PCR: (Perkin Elmer, 1994)). Such modifications included altering the concentration of $MgCl_2$, dNTPs, and primers in the PCR reaction mix, and adjusting experimental conditions, such as annealing temperature. Reagents were obtained from Gibco BRL Life Technologies, Gaithersburg, Md., and synthesized primers were obtained from Gibco BRL Life Technologies, Grand Island, N.Y.

Concentration of $MgCl_2$ was tested in first- and second-stage PCRs over a range from 1.0 mM, which resulted in no product, to 4 mM, which yielded many spurious products. Primer concentrations were tested in a first-stage (N1) PCR over a range of concentrations from 362 nM to 10.8 μM, with the lower value producing barely visible amplified products and the upper value producing no template. Primer concentrations were tested in a second-stage (N2) PCR over a range from 262 nM to 7.86 μM. Effect of dNTP concentration on the sensitivity of the nested PCR method was also tested. Decreasing concentrations of dNTP resulted in decreasing levels of sensitivity. Effect of annealing temperature on production of amplified product was also examined. The first-stage PCR resulted in no amplified products at annealing temperatures≧70° C. or at temperatures≧55° C. Additionally, a range of 25 to 45 cycles was found to maximize yield of amplified products (data not shown).

Based on these studies, the optimized concentrations for constituents in the N1 PCR master mix include 1×PCR buffer (20 mM Tris-HC1 (pH 8.4) and 50 mM KCl), 2.0 mM $MgCl_2$, 0.2 mM dNTPs, 3.56 μM of each primer, and 1.25 U Taq polymerase (Perkin-Elmer Cetus, Norwalk, Conn.) with a total reaction volume of 50 μl . The N2 PCR master mix was identical except for a primer concentration of 2.64 μM each. Sensitivity assays with the optimized reactions and 40 cycles for the N1 PCR and 35 cycles for the N2 PCR showed an ability to detect fewer than 20 copies of pseudorabies virus gII genome from a background of $2\times10^5$ porcine pancreatic cells on ethidium bromide stained agarose gels.

Example 5

Analysis of Specificity of the Nested PCR Assay for the Pseudorabies Virus

Electrophoresis of first-stage (N1) and second-stage (N2) PCR products obtained in Example 3 was done in the following manner: 9 μl of each PCR reaction was mixed with 3 μl of gel loading dye, and 10 μl was pipetted into a corresponding well of a 2% agarose gel stained with ethidium bromide. One lane on each gel contained a 100 bp ladder (Gibco BRL Life Technologies, Gaithersburg, Md.) as a set of molecular size standards.

Tonsilar tissues infected with pseudorabies virus and screened with the N1 PCR yielded an amplified product that migrated slightly forward of the 700 bp molecular size standard (FIG. 1). This is to be compared with the 674 base-pair product predicted with the use of the outer primer pair having the nucleotide sequences listed 5' to 3' by location as follows: 754—GCCCCGCACAAGTTCAA (upper primer; SEQ ID NO:2) and 1427—TCG TCG CGG GTC ATC TC (lower primer; SEQ ID NO:4). The same tissues subjected to both the first- and second-stage PCRs yielded an amplified product from the N2 PCR that migrated equidistant from the 500 bp and 400 bp molecular size standards (FIG. 2). This is to be compared with the 443 base-pair amplified product predicted with the use of the inner primer pair having the nucleotide sequences listed 5' to 3' by location as follows: 902—GCG GCA AGT GCG TCT CCA AGG (upper primer; SEQ ID NO:6) and 1344—CGT GAA GTG CGG CGT GCG TAG (lower primer; SEQ ID NO:11 ).

To confirm amplification of the gII region of the pseudorabies virus genome, restriction endonuclease (RE) digests were performed with Nar I [which hydrolyzes at the site GG'C.GCC (position 1064)] or Sma I [which hydrolyzes at the sequence CCC'GGG (position 1238)] as follows: 3 µl of each completed PCR reaction was mixed with 1 µl of either 10×React 1 (Nar I) or 10×React 4 (Sma I), 5 μl $H_2O$, and 1 μl of the appropriate RE (RE and buffers from Gibco BRL Life Technologies, Gaithersburg, Md.) in a 500 μl thin-walled reaction tube; the reactions were incubated at 37° C. for at least 3 hours; and electrophoresed as previously stated on 2% agarose gels stained with ethidium bromide. Nar I digestion of the N1 PCR amplified product (FIG. 3) yielded bands visible upon UV illumination that migrated one just below the 400 bp molecular size marker and the other just above the 300 bp marker. The Sma I digest yielded bands that migrated slightly below the 500 bp marker and just below the 200 bp marker. Nar I digestion of the N2 PCR amplified product (FIG. 4) yielded bands visible upon UV illumination that migrated one just below the 300 bp marker and one just below the 200 bp marker. The Sma I digest yielded bands that migrated one about midway between the 200 and 300 bp markers, and one just above the 100 bp marker. These patterns of restriction digest products were understood to be those predicted given the location of the upper and inner primers of the outer and inner primer pairs, thereby providing conformation of sequence identity.

In order to obtain further proof of sequence identity and to assess sensitivity issues safely (without the use of large quantities of virus), the N1 amplified product was cloned. T4 DNA ligase was used to insert the N1 amplified product into the pCR2.1 vector provided in a TA cloning kit (Invitrogen Corporation, Carlsbad, Calif.). INVaF'*E. coli* cells, also provided in the TA cloning kit, were then transformed with the transformation vector. The transformants were plated on LB agar (50 μg/ml ampicillin and 40 μg X-Gal) and incubated overnight at 37° C. Sixtcen white colonies were harvested and grown overnight in 5 ml LB broth in a 37° C. incubator while shaking at 225 rpm. The plasmids were isolated via a plasmid DNA mini-prep (Sambrook et al. (1989) *Molecular Cloning: A Laboratory Manual* (2d ed.; Cold Spring Harbor Laboratory Press: Plainview, N.Y.). Isolated plasmid DNA was quantified via UV spectrophotometry as in Example 2. Subsequent treatment of isolated plasmid DNA with an EcoR I digest excised the inserted N1 amplified product by cutting at the two unique EcoR I sites that flank the insert. The resulting DNA inserts were analyzed by agarose gel electrophoresis as in Example 3. Five of the 16 plasmids were shown to contain the N1 amplified product (data not shown). Two of those were utilized in sensitivity assays (N11312 and N11313).

Example 6

Analysis of Sensitivity of the Nested PCR Assay for the Pseudorabies Virus

Plasmid N11312 was linearized via restriction enzyme digest with Xba I (recognizes the sequence TCT' AGA found once in the plasmid and not in the insert) to make it more representative of the linear PRV genome. Serial dilutions of the linearized plasmid were then introduced into the NI PCR reaction at total concentrations of from 1.1 attograms to 110 picograms in 10-fold increments. Included as positive control was infected tonsil DNA and as negative controls pancreas DNA and a water-only control. An aliquot of the end result from reaction N1 was introduced into reaction N2, and the second PCR reaction run as specified. Samples of the resulting N2 reaction results were run on agarose gels stained with ethidium bromide.

In this series, specific signal was obtained from all test reactions that received more than 11 attograms of template as well as the tonsil positive control (FIG. 5). Inappropriate-sized bands or none at all were obtained from the other reaction mixtures.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A kit for detecting the presence or absence of pseudorabies virus in a sample using a nested polymerase chain reaction, said kit comprising at least two nucleotide sequences for an outer pair of oligonucleotide primers used in a first-stage polymerase chain reaction, and at least two nucleotide sequences for an inner pair of oligonucleotide primers used in a second-stage polymerase chain reaction, wherein said outer pair and inner pair of primers each consist of a 5' upper primer and a 3' lower primer, wherein the nucleotide sequence comprising the upper primer of the outer primer pair is SEQ ID NO: 2, the nucleotide sequence comprising the lower primer of the outer primer pair is selected from the group consisting of SEQ ID NOS: 3 to 4, the nucleotide sequence comprising the upper primer of the inner primer pair is selected from the group consisting of SEQ ID NOS: 5 to 7, and the nucleotide sequence comprising the lower primer of the inner primer pair is selected from the group consisting of SEQ ID NOS: 8 to 11.

2. The kit of claim 1, wherein said sample is porcine tissue.

3. The kit of claim 1, wherein the nucleotide sequence comprising the lower primer of the outer primer pair is SEQ ID NO: 4, the nucleotide sequence comprising the upper primer of the inner primer pair is SEQ ID NO: 6, and the nucleotide sequence comprising the lower primer of the inner primer pair is SEQ ID NO: 11.

4. The kit of claim 3, wherein said sample is porcine tissue.

5. A nucleotide sequence comprising a 5' upper primer of an outer pair of oligonucleotide primers used in a first-stage polymerase chain reaction, said upper primer being derived from a 674 base-pair region of the pseudorabies virus gII glycoprotein gene, said 674 base-pair region having the nucleotide sequence set forth in SEQ ID NO:1, wherein said sequence is SEQ ID NO:2.

6. A nucleotide sequence comprising a 3' lower primer of an outer pair of oligonucleotide primers used in a first-stage polymerase chain reaction, said lower primer being derived from a 674 base-pair region of the pseudorabies virus gII glycoprotein gene, said 674 base-pair region having the nucleotide sequence set forth in SEQ ID NO:1, wherein said sequence is selected from the group consisting of SEQ ID NOS:3 to 4.

7. The nucleotide sequence of claim 6, wherein said sequence is SEQ ID NO:4.

8. A nucleotide sequence comprising a 5' upper primer of an inner pair of oligonucleotide primers used in a second-stage polymerase chain reaction, said upper primer being derived from a 674 base-pair region of the pseudorabies virus gII glycoprotein gene, said 674 base-pair region having the nucleotide sequence set forth in SEQ ID NO:1, wherein said sequence is selected from the group consisting of SEQ ID NOS:5 to 7.

9. The nucleotide sequence of claim 8, wherein said sequence is SEQ ID NO:6.

10. A nucleotide sequence comprising a 3' lower primer of an inner pair of oligonucleotide primers used in a second-stage polymerase chain reaction, said lower primer being derived from a 674 base-pair region of the pseudorabies virus gII glycoprotein gene, said 674 base-pair region having the nucleotide sequence set forth in SEQ ID NO:1, wherein said sequence is from the group consisting of SEQ ID NOS:8 to 11.

11. The nucleotide sequence of claim 10, wherein said sequence is SEQ ID NO:11.

\* \* \* \* \*

UNITED STATES PATENT AND TRADEMARK OFFICE
CERTIFICATE OF CORRECTION

| | | |
|---|---|---|
| PATENT NO. | : 6,270,977 B1 | Page 1 of 1 |
| DATED | : August 7, 2001 | |
| INVENTOR(S) | : Klann | |

It is certified that error appears in the above-identified patent and that said Letters Patent is hereby corrected as shown below:

<u>Title page</u>,
Insert -- Related U.S. Application Data
[60] Continuation of Application No. 09/069,811, filed April 29, 1998, now Patent No. 6,068,974. --

Signed and Sealed this

Twelfth Day of March, 2002

Attest:

Attesting Officer

JAMES E. ROGAN
*Director of the United States Patent and Trademark Office*